United States Patent [19]

Hulka

[11] Patent Number: 4,537,197
[45] Date of Patent: Aug. 27, 1985

[54] DISPOSABLE FETAL OXYGEN MONITOR

[76] Inventor: Jaroslav F. Hulka, 2317 Honeysuckle Rd., Chapel Hill, N.C. 27514

[21] Appl. No.: 241,433

[22] Filed: Mar. 6, 1981

[51] Int. Cl.³ .............................................. A61B 5/00
[52] U.S. Cl. .................................. 128/633; 128/361; 128/398
[58] Field of Search ............... 128/306, 307, 361, 633, 128/664, 665, 666, 670, 784, 785, 642, 234; 356/39, 40, 41

[56] References Cited

U.S. PATENT DOCUMENTS

| 73,402 | 1/1868 | Sornborger | 128/234 |
|---|---|---|---|
| 3,461,856 | 10/1965 | Polanyi | 356/41 |
| 3,765,408 | 10/1973 | Kawai | 128/361 |
| 3,866,599 | 2/1975 | Johnson | 356/41 |
| 4,029,085 | 6/1977 | DeWitt et al. | 128/633 |
| 4,299,232 | 11/1981 | Zilianti | 128/642 |

FOREIGN PATENT DOCUMENTS 738598  8/1980  U.S.S.R. ................ 128/634

*Primary Examiner*—Kyle L. Howell
*Assistant Examiner*—Karin M. Reichle
*Attorney, Agent, or Firm*—Kinzer, Plyer, Dorn & McEachran

[57] ABSTRACT

Oxygenation within the brain of a child being born is monitored by light, initially transmitted by a bundle of fiber optics in one channel of a catheter held to the baby's scalp by mild suction, the condition of the brain being monitored via reflected light from the brain transmitted through a light fiber optic bundle in a second channel of the catheter.

3 Claims, 4 Drawing Figures

U.S. Patent  Aug. 27, 1985  4,537,197
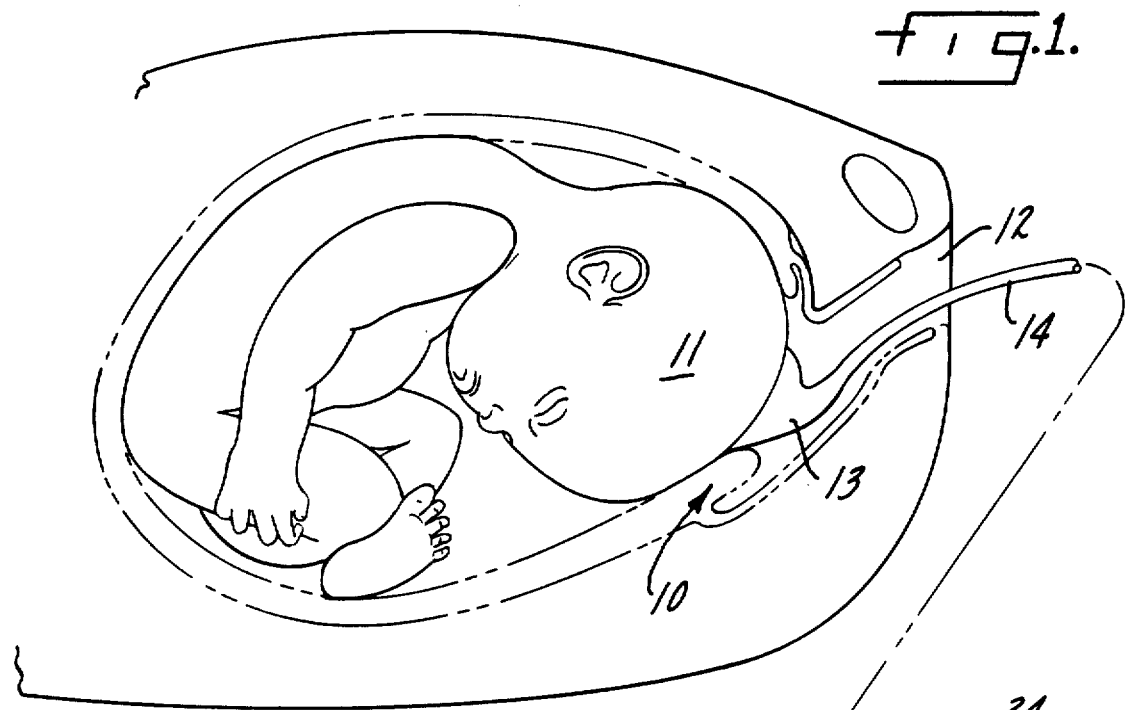
fig.1.
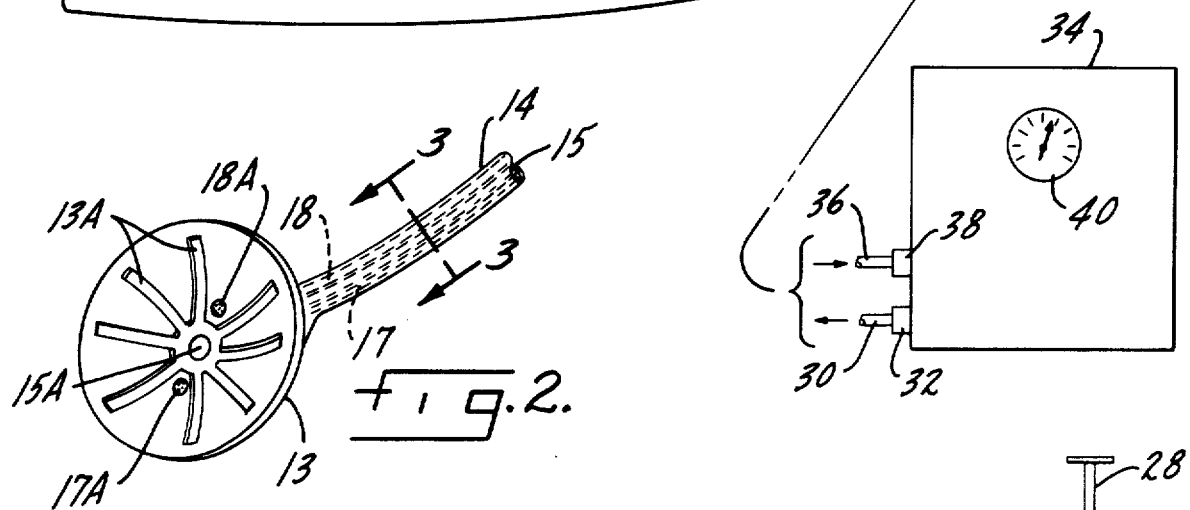
fig.2.
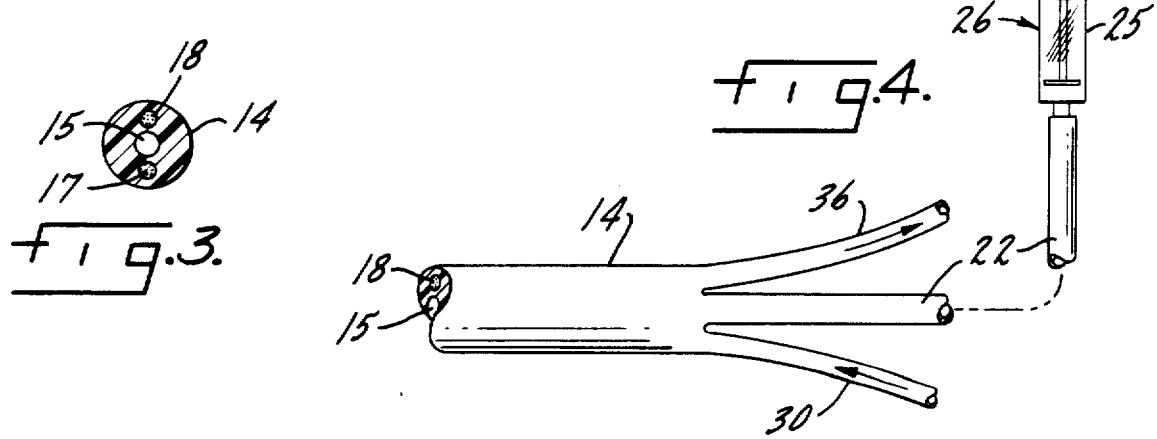
fig.3.
fig.4.

DISPOSABLE FETAL OXYGEN MONITOR

INTRODUCTION AND BACKGROUND

Currently all hospitals are medicolegally compelled to monitor women in labor to assure fetal well-being. This is accomplished by detecting fetal heart sounds by ultrasound electronics, or by direct recording of the fetal electrocardiographic impulses by inserting a fetal scalp monitor by wire into the scalp. Both of these do no more than indicate the heart rate of a baby, which is one of the last things to change in a case where the baby is gradually being deprived of oxygen.

Direct measures of oxygenation of tissues are possible by light delivered through the skull, filtering out back reflections except those from beyond a certain depth (2 or 3 inches into the head) and monitoring the reflected light for enzymatic changes and the color-sensitive changes of blood to determine the degree of oxygen deprivation in the blood and tissues. This sophisticated technique is currently being developed in collaboration by the University of North Carolina and Duke University departments of Bio-Engineering and Surgical Trauma. It is currently under contract by the United States Navy.

The actual monitoring consists simply of sending a beam of light into the scalp by one glass fiber bundle and measuring the back-scatter of this beam returned by a separate glass fiber bundle. These fiber bundles need be only large enough to transmit sufficient light for penetration and back-scatter. The current prototype for adult trauma cases where there may be interference with oxygenation because of head, heart, or lung injuries involves a fairly stiff half-inch cable held to the head by a strap.

THE OBJECTS OF THE PRESENT INVENTION

With the foregoing as background and the best prior art known to me, one object of the invention is to develop obstetrical equipment permitting oxygenation in the brain of the fetus to be observed during the process of labor and delivery.

Another object of the invention is a disposable fetal scalp cap and attached three-channel catheter.

Specifically, another object is that of monitoring of the fetus during labor, where the baby has progressed through the cervix to the point that the baby's head is accessible through the vagina, by a fetal monitor of flexible plastic provided with two fiber bundles presented to the fetal scalp, one for transmitting light and one for receiving it; and to hold this plastic light source onto the scalp, a series of recesses or grooves are formed in the plastic scalp portion, leading to a channel which exerts a mild vacuum pressure generated by a plastic syringe outside the patient. The light bundles are interfaced to the oxygen level analysis equipment and suction is then applied to the scalp cap so that continuous analysis may be made during childbirth.

IN THE DRAWING:

FIG. 1 is a pictorial representation of a baby in birth, being monitored in accordance with the present invention;

FIG. 2 is a fragmentary detail view of the scalp cap and catheter;

FIG. 3 is a sectional view of the catheter on the line 3—3 of FIG. 2;

FIG. 4 is a detail elevational view of the catheter.

At the time of labor, incidental to delivery, the cervix 10, FIG. 1, will be open by about two cm. or perhaps more as part of the mother's natural delivery processes, so that the scalp 11 of the fetus is available to the physician through the vagina 12. Consequently, the operating physician, who has available the monitor equipment, can apply to the baby's scalp a cap or cup 13 of soft plastic.

The cap 13 when attached to the baby's scalp is to be held there by very mild suction and to this end the concave side or inner surface of the cap is communicated to a plastic catheter 14 attached to the outside or convex surface of the cap and indeed the cap and tube or catheter may be comolded as a one-piece soft plastic assembly.

To assure effective application of suction the inside surface of the cap is provided with channels or recesses 13A, FIG. 2, each at one end communicating with the open end 15A of a central passage 15 in the plastic catheter. This passage is adapted to be connected at its opposite end to a source of mild vacuum as will be explained; the opposite ends of the recesses 13A are closed to trap the vacuum between the cap and scalp, and of course by vacuum I mean negative atmosphere pressure.

To monitor the oxygen supply to the brain at the time of delivery of the child light is transmitted via a fiber optic bundle in catheter 14 to penetrate the skull to a depth where enzymatic activity associated with normal oxygenation in (or of) the brain cells will be evident from the reflected light; a return fiber optic bundle gathers the scattered light within the area of the brain involved and returns it so the return light may be instantly analyzed. It may be mentioned that cell enzymes in a healthy state of oxygenation use enzymes in a process known as "aerobic oxidation" for cell metabolism; when oxygen is not available the aerobic enzymes cease activity and "anerobic oxidation" assumes an active role. This change in activity may be measured by colorometric techniques and is the monitor technique I prefer for monitoring oxygenation levels in the fetal brain.

Thus, as shown in the drawing, the catheter in addition to the channel 15 for vacuum, includes a pair of channels housing, respectively, a bundle of optic fibers 17 for transmitting light to terminal aperture 17A at the inside surface of the scalp cap and a second bundle 18 of like optic fibers for receiving return light waves at the terminal aperture 18A. The return light waves may or may not be altered as to characteristic, depending upon the state of oxygenation of (or in) the child's brain.

The proximal end of the catheter opposite the scalp cap may be split into three branches including a branch 22 which communicates at its free end with the interior or cylinder 25 of a syringe 26. The syringe has a catch (not shown) on its plunger or piston inside the cylinder such that upon withdrawing the piston by the plunger handle 28 a vacuum may be communicated through the length of the catheter to port 15A to the recesses of the scalp; the catch will hold against the cylinder.

The branched catheter includes a second branch 30 connected to a related fiber optic outlet 32 for receiving light from an electronic transmitter (not shown) inside a case or housing 34 to which the outlet 32 is attached.

The catheter has a third branch 36 connected to a related fiber optic outlet 38 on the housing 34 and by this connection the branch 36 transmits the return wave light from the monitored brain.

The back-scatter or return light will be altered by color-specific enzymatic or chemical changes directly related to oxygenation of the tissues being monitored in the brain. The return light in the optic bundle in branch 36 may therefore be analyzed for oxygenation of the tissues and this is accomplished by known equipment inside housing 34 to determine the degree, if any, of oxygen deprivation in the fetus. The analysis is shown by a dial 40 (or equivalent readout device) calibrated to the specific type of oxygenation level being monitored.

Thus, the source of light at outlet 32 is transmitted through the catheter to the brain by means of the vacuum-held scalp cap and the reflected light, altered by the reflectance or transmittal character of the brain tissues being monitored, is reflected back through the branch 36 so the physician can observe the dial pointer 40 for a safe level of oxygenation. The mild but effective vacuum assures reliable contact between the baby's scalp and the fiber ends 17A,18A.

The soft scalp cap and comolded catheter 14 may be manufactured and packaged as a sterilized unit per se, ready for clinical use only when the package is opened by the physician in the obstetric role, ready for delivery. Thus, after the monitor sequence described above has been completed the branches of the catheter are disconnected from the parts to which they are attached and the scalp cap and comolded catheter are disposed of, avoiding the risk and expense of cleaning and sterilizing for reuse.

There is nothing critical about the arrangement of the slots or recesses 13A, nor is it necessary that the catheter be branched and interfaced as it is to the particular source of vacuum and the optic attachments 32 and 38. However, a syringe is certainly a safe way to effect a mild vacuum, and the fewer the fittings or attachments the more efficient is the transfer of light via fiber optics.

I claim:

1. Surgical equipment comprising an obstetrical scalp cap of soft flexible plastic to be attached to a fetal scalp incidental to monitoring oxygenation of the fetal brain tissue, said cap having on its inner surface one or more recesses communicating with a port in the cap by which vacuum may be delivered thereto to hold the scalp cap in place at the time of expected delivery, said scalp cap including a pair of apertures at the inner surface, and a comolded catheter on the outside of the cap, said catheter having a channel for communicating vacuum to said port and having a pair of channels respectively accommodating fiber optic bundles by which a beam of light may be transmitted to the fetal brain through one of said pairs of apertures and reflected back through the other.

2. Surgical equipment according to claim 1 in which the vacuum channel in the end of the catheter opposite the scalp cap has vacuum communicated thereto by a syringe.

3. Surgical equipment according to claim 1 or 2 in which the ends of the fiber optic bundles opposite the apertures related thereto are respectively connected to a light beam transmitter and an instrument for analyzing the reflected light in terms of the oxygenation equivalent.

* * * * *